US009678001B2

(12) United States Patent
Zhao et al.

(10) Patent No.: US 9,678,001 B2
(45) Date of Patent: Jun. 13, 2017

(54) ROUTE-BASED SUBSTANCE ANALYSIS SYSTEM AND METHOD

(71) Applicant: Spectro Scientific, Inc., Chelmsford, MA (US)

(72) Inventors: Yuegang Zhao, Andover, MA (US); Raymond E. Garvey, III, Loudon, TN (US); Robert David Corak, Franklin, MA (US); Eric J. Olson, Phillipston, MA (US); Matthew B. Fratkin, Brookline, MA (US); Patrick Henning, Concord, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 0 days.

(21) Appl. No.: 14/090,685

(22) Filed: Nov. 26, 2013

(65) Prior Publication Data
US 2014/0151560 A1    Jun. 5, 2014

Related U.S. Application Data

(60) Provisional application No. 61/731,559, filed on Nov. 30, 2012.

(51) Int. Cl.
*G01N 21/35*    (2014.01)
*G01N 21/3577*  (2014.01)
(Continued)

(52) U.S. Cl.
CPC ......... *G01N 21/3577* (2013.01); *G01N 33/28* (2013.01); *G01N 21/552* (2013.01); *G01N 2201/0221* (2013.01)

(58) Field of Classification Search
CPC . G01N 33/2888; G01N 21/3577; G01N 33/30
(Continued)

(56) References Cited

U.S. PATENT DOCUMENTS 5,386,117 A    1/1995  Piety et al.
5,420,041 A    5/1995  Matsushita et al.
(Continued)

FOREIGN PATENT DOCUMENTS

| CN | 1991336 A | * | 7/2007 |
| CN | 100547385 C | * | 10/2009 |
| CN | 202305391 U | | 7/2012 |

OTHER PUBLICATIONS

"Lube Routes vs. Combo PMs: What's Best? What Are the Issues?", http://www.machinerylubrication.com/Read/2347/lube-routes-pm, Noria Corporation, Machinery Lubrication, Sep. 2009, 3 pgs.
(Continued)

*Primary Examiner* — Marcus Taningco
(74) *Attorney, Agent, or Firm* — Iandiorio Teska & Coleman, LLP

(57) ABSTRACT

A route based analysis system includes, in one version, an infrared spectrometer subsystem configured to produce a spectrum for oil introduced to an oil sample cell. The system displays a route including assets with oil to be inspected. The type of oil used in each asset is determined. For each asset on the route, one or more oil property methods specific to the oil used in the asset are located. The spectrum of each asset's oil is analyzed using specific methods in order to produce oil properties.

19 Claims, 8 Drawing Sheets

(51) Int. Cl.
G01N 33/28 (2006.01)
G01N 21/552 (2014.01)

(58) Field of Classification Search
USPC .................................................. 250/339.07
See application file for complete search history.

(56) References Cited

U.S. PATENT DOCUMENTS

| | | | |
|---|---|---|---|
| 5,637,871 | A | 6/1997 | Piety et al. |
| 5,764,355 | A | 6/1998 | Gagnon et al. |
| 5,856,870 | A | 1/1999 | Curtiss |
| 6,192,325 | B1 | 2/2001 | Piety et al. |
| 6,289,149 | B1 | 9/2001 | Druy et al. |
| 7,254,501 | B1 | 8/2007 | Brown et al. |
| 7,454,050 | B2 | 11/2008 | Garvey |
| 7,495,761 | B2 | 2/2009 | Chadha et al. |
| 7,528,372 | B2 | 5/2009 | Garvey, III et al. |
| 7,561,200 | B2 | 7/2009 | Garvey, III et al. |
| 7,698,080 | B2 | 4/2010 | Brown et al. |
| 7,706,596 | B2 | 4/2010 | Garvey |
| 7,902,507 | B1 | 3/2011 | Garvey, III et al. |
| 8,148,687 | B1 | 4/2012 | Praly |
| 8,242,445 | B1 | 8/2012 | Scanlon et al. |
| 8,384,895 | B2 | 2/2013 | Albin et al. |
| 8,661,878 | B2 | 3/2014 | Henning et al. |
| 2009/0240640 | A1* | 9/2009 | Blain et al. ..................... 706/12 |
| 2010/0134794 | A1 | 6/2010 | Odegard et al. |
| 2010/0182599 | A1 | 7/2010 | Albin et al. |
| 2013/0191046 | A1* | 7/2013 | Henning et al. ................ 702/50 |
| 2014/0002809 | A1 | 1/2014 | Greere et al. |

OTHER PUBLICATIONS

"IR: What's A Survey? What's A Route", http://www.reliableplant.com/article/print/3721, Ray Garvey, Reliable Plant, Nov. 2006, 5 pgs.

International Searching Authority, Written Opinion of International Application No. PCT/US13/72197, Apr. 28, 2014, 7 pgs. (unnumbered).

Forteza, M., "Using Oil Analysis and Daily Inspections to Improve Lubrication", Machinery Lubrication, Oct. 2012, <URL; http://www.machinerylubrication.com/Read/29122/inspections-improve-lubrication>, 6 pgs.

OilView™ AMS Suite: Machinery Health™ Manager In-Shop Oil Analysis and Laboratory Information Management System, Reference Manual, Emerson Process Management, © 2012, four hundred forty-six (446) pages.

Fluid Scan Q1100 FL356 Operator's Guide, Rev. C, Jun. 2014, Spectro Scientific, Inc., eighty-two (82) pages.

SpectroVisc Q3000 Kinematic Viscometer User's Guide V1.3, 2012, Spectro, Inc., thirteen (13) pages.

Q5800, 34683145 User's Guide, Rev. A, May 2014, Spectro Scientific, one-hundred twenty (120) pages.

Thermo Scientific, MicroPHAZIR RX, Product Specifications, Thermo Scientific, © 2010, two (2) pages.

Thermo Scientific TruDefender FT and TruDefender FTi , Product Specifications, Thermo Scientific, © 2012, two (2) pages.

Thermo Scientific FirstDefender RM, Product Specifications, Thermo Scientific, © 2012, two (2) pages.

Spectro 5200 Trivector™ Analyzer, Product Specification, Spectro Inc., © 2012, two (2) pages.

Bruker S1 Titan, specification sheet, Bruker, downloaded Feb. 17, 2012, four (4) pages.

MetalScan On-Line Oil Debris Monitor, Specifications, Gastops Ltd., downloaded Apr. 18, 2013, one (1) page.

ANALEXpq, Ferrous Debris Monitors, Kittiwake Developments Ltd., downloaded Jun. 10, 2010, six (6) pages.

OSA Microlab, Product Specifications, Spectro Scientific, Inc., © 2015, two (2) pages.

SpectroTrack Client Reference Guide, Spectro, Inc., © 2012, thirty-two (32) pages.

ASTM Designation: D7889-13, Standard Test Method for Field Determination of In-Service fluid Properties Using IR Spectroscopy, © Oct. 24, 2013, eight (8) pages.

ASTM Designation: D7416-09, Standard Practice for Analysis of In-Service Lubricants Using a Particular Five-Part (Dielectric Permittivity, Time-Resolved Dielectric Permittivity with Switching Magnetic fields, Laser Particle Counter, Microscopic Debris Analysis, and Orbital Viscometer) Integrated Tester, © May 2012, thirteen (13) pages.

ASTM Designation: D7417-10, Standard Test Method for Analysis of In-Service Lubricants Using Particular Four-Part Integrated Tester (Atomic Emission Spectroscopy, Infrared Spectroscopy, Viscosity, and Laser Particle Counter), © Dec. 2010, nine (9) pages.

ASTM Designation: D6595-00 (Reapproved 2011), Standard Test Method for Determination of Wear Metals and Contaminants in Used Lubricating Oils or Used Hydraulic Fluids by Rotating Disc Electrode Atomic Emission Spectrometry, © Apr. 2014, six (6) pages.

TotalOil Operator's Guide, Part No. OPM6000, Spectro, Inc., 2012, fifty-eight (58) pages.

OSA Oil Analyzer System, Technical Specifications, On-Site Analysis, Inc., Jan. 12, 2012, eight (8) pages.

ASTM Designation: D6595-00 Standard Test Method for Determination of Wear Metals and Contaminants in Used Lubricating Oils or Used Hydraulic Fluids by Rotating Disc Electrode Atomic Emission Spectrometry, downloaded Jan. 3, 2007, five (5) pages.

Marc Vila Forteza, Machinery Lubrication, http://www.machinerylubrication.com/Read/29122/inspections-improve-lubrication (Oct. 10, 2012) seven (7) pages.

Han Qingtian et al., Maintenance Route Planning Based on Particle Swarm Optimization Algorithm, 2012 International Conference on Computer Science and Electronics Engineering, 2012 IEEE pp. 195-198.

* cited by examiner

Route Management

Select Route

| Status | Route |
|---|---|
| | <Import New Route...> |
| New | Mill 1 Standard |
| Completed | Mill 2 Special |
| In Progress | Mill 3 Special |

[ Delete ] [ Main Menu ] [ Open ]

*FIG. 5A*

Route: Mill 1 Standard

Route Item

- Finish Area 1/Blade Former/Gearbox DTE
- Service/Backup/Generator Rotella
- Main Prod/Main Former/Turbine Turbo 32
- Main Prod/Hot Line/Hydro Fyrquel Details:
Sample ID:    4893636
Substance:    DTE
AEP:          Finish Area 1/Blade Former/Gearbox
Unit ID:      Renamzar, TA, Oil Mach 1.P1

[ Hide Done ] [ Main Menu ] [ Back ] [ Measure ]

ROUTE-BASED SUBSTANCE ANALYSIS SYSTEM AND METHOD

RELATED APPLICATIONS

This application claims benefit of and priority to U.S. Provisional Application Ser. No. 61/731,559 filed Nov. 30, 2012 under 35 U.S.C. §§119, 120, 363, 365, and 37 C.F.R. §1.55 and §1.78 and the entirety of which is fully incorporated herein by this reference.

FIELD OF THE INVENTION

The invention relates to route based inspections and, in one particular example, an easy to use route based infrared spectrometer oil analysis system.

BACKGROUND OF THE INVENTION

Route based inspections provide for a fully documented inspection with automatic reporting. See "IR: What's a Survey? What's a Route?", Ray Garvey, http://www.reliableplant.com/article/print/3721; Noria Corporation, "Lube Routes vs. Combo PMs: What's Best? What Are the Issues?" http://www.machinerylubrication.com/Read/2347/lube-routes-pm; and Marc Vila Forteza, "Using Oil Analysis and Daily Inspections to Improve Lubrication", http://www.machinerylubrication.com/Read/29122/inspections-improve-lubrication incorporated herein by this reference. Route based inspections have been used in connection with vibration analysis and infrared cameras. Field-based attributes using infrared spectrometers and similar devices have been used to determine compositional attributes of a sample. See also U.S. Pat. Nos. 7,698,080, 7,454,050, 7,254,501, 5,637,871, and 5,386,117 all incorporated herein by this reference.

SUMMARY OF THE INVENTION

To date, no one has successfully implemented infrared spectroscopy or similar inspection methods in a route based inspection system.

One possible reason is that IR spectroscopy is complex and highly sensitive. Also, a given facility may include a number of different assets (sometimes 1,000 or more) each including a different lubricating oil. In one preferred system, reference spectrums for each oil are used. Also, different assets have different alarm limits. For example, the oil used in a gas turbine engine may be quite different than the oil used in a diesel generator and both machines have quite different alarm limits, or another gas turbine engine for that matter.

Analyzing the spectrum of each asset's oil, if performed the same way for each asset and each type of oil, may lead to frequent false negatives meaning the oil in an asset in a route based inspection is reported as being within tolerances when it is not resulting in a possible threat to the asset.

In the invention, the user need not concern herself/himself with choosing differently weighted convolution functions or wavelength regions for the proper analysis of different oils. Instead, the user follows the route displayed to him, loads the unit's sample cell with oil from an asset at each inspection point, initiates the automatic computerized analysis methods, and notes any reported alai indications.

The invention provides a method and apparatus to avoid or reduce human error introduced during oil sampling and analysis through the use of programmed logic to correctly identify a testing technique and an out-of-limit level and reliance on the human inspector to correctly identify the measurement point in the field.

This applies to an inspector walking around a plant with fixed assets, or it applies to an inspector in a service bay where mobile fleet assets come to into the bay from time to time.

Featured is a route based analysis system comprising an oil sample cell, an infrared spectrometer subsystem configured to produce a spectrum for oil introduced to the oil sample cell, and processing subsystem. The processing subsystem is configured to display a route including assets with oil to be inspected, determine the type of oil used in each asset, locate, for each asset on the route, one or more oil property methods specific to the oil used in the asset, and locate, for each asset along the route, an alarm set specific to the asset. The route itself may be time-based, previous condition-based, specified by the user, or determined by artificial intelligence in the processing subsystem itself to produce an adaptive route. Such a system enables planned coverage of an entire range of assets based on economic and ROI considerations which may be factored by the processing subsystem.

The processing subsystem then analyzes the spectrum of each asset's oil using the located specific methods and calculates and produces oil properties after introducing the oil to the sample cell along the route. These oil properties are compared with the alarm set specific to the asset, and the oil properties and any alarm indications are displayed.

In one preferred embodiment, the processing subsystem locates, for each asset's oil, a reference spectrum. Analyzing may include using oil property methods which compare the produced spectrum with the reference spectrum. Preferably, different oil property methods cover different spectrum wavelength ranges and different oil property methods include differently weighted functions such as convolution functions. Typical displayed oil properties include water content, acidity, soot content, the presence of additives, and/or percent oxidation, and/or combinations of the same. The properties may further include, for select assets, a calculated total acid and/or saponification number. The oil properties may include, for other assets, a total base number.

In one example, the sample cell is a flip-top sample cell. A portable, hand held unit may include a screen for the displayed information. In some examples, the type of oil used in each asset on the route, the oil property methods, and the alarm sets are stored in a hand held, portable unit.

Note that a sample cell in this example is effectively a confined volume of oil sample between two windows. However, a sample cell may be generalized to include other sensing configurations for producing a sensory engagement with a specimen of interest. Also, bringing specimen of interest to a sample cell is effectively the same as bringing a sample cell the specimen of interest. According to the present invention a sample cell may receive a specimen of interest or a sample cell may be delivered to a specimen of interest.

Also featured is a route based analysis method comprising displaying a route including assets with oil to be inspected, determining the type of oil used in each asset, locating, for each asset on the route, one or more oil property methods specific to the oil used in the asset, and locating, for each asset along the route, an alarm set specific to the asset. Oil from an asset on the route is loaded into a sample cell. An infrared spectrum for the oil introduced to the oil sample cell is produced and analyzed using the oil type specific methods to calculate and produce oil properties. These oil properties are compared with the alarm set specific to the asset and displayed.

Also featured is an analysis system and method comprising an analysis subsystem configured to analyze a substance introduced to a sample cell and a processing subsystem. The processing subsystem is configured to: determine the type of substance associated with an asset, locate, for each asset, one or more analysis methods specific to the substance used in the asset, and analyze the asset's substance using the located analysis methods producing at least one property after introducing the substance to the sample cell.

A route based oil analysis typically involves a cleaning step. The cleaning step is typically intended to return a sample cell to a satisfactory condition, ready to make sensory contact with a new specimen. It is important to assure that a next measurement will not be adversely affected by a residue of a previous specimen or a residue of a cleaning material. Common cleaning process examples are a wipe or a flush or a drain or a drying or a combination of two or more of these. It is also common for a compensation step or a "clean-check" step to be performed to further remove measurement from adverse influence of cross contamination, residue, or other environmental or physical change from day to day or test to test.

In one version, the processing subsystem is further configured to locate, for each asset, an alarm set specific to the asset, and to display one or more alarm indications based on the alarm set. The substance, in one example, is oil and the analysis subsystem is, in one example, an infrared spectrometer producing a spectrum for oil introduced into the sample cell. The processing subsystem may be configured to locate, for each asset's oil, a reference spectrum and analyzing includes using oil property methods which compare the produced spectrum with the reference spectrum. The methods preferably cover different spectrum wavelength ranges and use differently weighted functions for different oils. In one route-based embodiment, the processing subsystem is further configured to use route data to display a route including assets to be inspected along a route. The route data is linked to the oil types, asset information, alarm limits, reference spectrums, and the like.

The route based oil analysis method avoids or reduces human error. One method comprises using a hand held, portable route based analysis unit with an oil sample cell (e.g., Transmission, ATR, reflectance, DRIFT, etc.) and an infrared spectrometer subsystem configured to produce a spectrum for oil introduced to the oil sample cell. The method may use a plurality substance IDs wherein a substance ID further comprises a designation representing a lubricant product or a group of lubricant products that produce a similar infrared spectroscopic measurement result when tested using a particular spectroscopic technique wherein a spectroscopic technique is a defined spectroscopic feature extraction technique. The method may further use a plurality of threshold values associated points wherein a threshold value represents an out-of-limit level for a characteristic from the group comprising a chemistry characteristic, a contamination characteristic, or a wear characteristic. The method may include programming an electronic memory with a structured database with a plurality of separated points, assigning a relevant substance ID and a characteristic out-of-limit level to each point in the plurality of points in the structured database, using programmed logic to assist an inspector with constructing a preferred route through at least a portion of the points in the structured database, using programmed logic guide a user to find a specific point within the group comprising the route or the database, using programmed logic to interpret the substance ID of the point and from that information determine the assigned spectroscopic technique and the out-of-limit level, and using programmed logic applies the correctly selected spectroscopic technique and out-of-limit level when testing and reporting the characteristic results from a specimen from the point with the infrared spectrometer.

An apparatus may be used by an in-field inspector to identify an oil compartment, test a specimen from the compartment and to ascertain possible misapplication or degradation. Such an apparatus may comprise a programmed spectrometer having a specimen test cell, a display, a microprocessor, a user input, and a memory, wherein the memory is programmed with a structured database having a plurality of points representing specimen collection points and a substance ID and an out-of-spec level is assigned to each point. Each substance ID may be a designation from a differentiated first and second substances designation, wherein a substance designation is an identifier for one lubricant product or for a group of lubricant products yielding a similar measurement result when tested using a relevant test sequence and feature extraction technique. First, second, and third lubricant product identifiers correspond to differentiated lubricant products. First, second, and third lubrication compartment identifiers correspond to differentiated equipment. First and second testing configurations wherein each yield repeatable results from testing the first substance and each yield a different repeatable result when testing the second substance. First and second out-of-spec levels corresponding to the first and second lubrication compartment. The programmed spectrometer assists an inspector with locating a point in the field and the programmed spectrometer uses programmed logic operating on information derived from operator locating a point to perform the preselected spectrometric test sequence and feature extraction technique and to apply the correct out-of-spec level when comparing results.

An apparatus used by an in-field inspector may further comprise differentiated lubricant products where the first lubricant product is a first hydraulic fluid from a first manufacturer of hydraulic fluids. The second lubricant is a specific heavy duty diesel engine oil from a specific manufacturer of heavy duty diesel engine oils. Third lubricant is a second hydraulic fluid from a second manufacturer of hydraulic oils equipment where the first compartment is pressurized line leading from a hydraulic pump to a hydraulic mechanism, the second compartment is an engine crankcase on a mobile machine, the third compartment is a storage compartment. The first configuration is a configuration for testing hydraulic oils but not for testing engine oils and the second configuration is a configuration for testing engine oils but not for testing turbine oils. The first level may be a 0.4 increase in TAN for the first oil compartment and the second level may be a 50% decrease in TBN for the second oil compartment. The first and third lubricant products can be tested and shown to pass a first substance designation criteria and to fail a second substance designation criteria. The second lubricant product is tested and shown to fail a first substance criteria and to pass a second substance designation criteria.

One sample point based oil analysis method reduces error by using programmed logic to correctly identify a testing technique for use with an oil tester and an out-of-limit level based on an identification of a measurement point in the field. One method comprises using a plurality substance IDs, wherein a substance ID further comprises a designation representing a lubricant product or a group of lubricant products that produce a similar measurement result when tested using particular measured data feature extraction technique. The method may use a plurality of threshold values associated points wherein a threshold value represents an out-of-limit level for a characteristic. The method may further include programming an electronic memory with a structured database with a plurality of separated points, assigning a relevant substance ID and a characteristic out-of-limit level to each point in the plurality of points in the structured database, using programmed logic guide a user to find a specific point within the database, using programmed logic to interpret the substance ID of the point and from that interpretation determine the assigned extraction technique and the out-of-limit level, and using programmed logic applies the correct extraction technique and out-of-limit level when testing and reporting the characteristic result from a test of a specimen from the point with the oil tester.

The substance ID feature extraction technique incorporates data measured from a new substance specimen. The similar measurement result may be a number for comparison with a tolerance. The characteristic is typically from a group comprising: a total base number characteristic, a total acid number characteristic, an oxidation characteristic, a water-in-oil characteristic, an anti-wear additive characteristic, and an anti-oxidant characteristic, ferrous particle measurement, a nonferrous metal particle measurement, a particle contamination measurement, and an element PPM measurement.

The separated points may be separated points from a group of separated points comprising: spatially separated points such as in a plant having stationary assets, temporally separated points such as in a service bay where mobile fleet equipment periodically visits, or spatially and temporally separated points such combination of both stationary and mobile equipment. The guide a user to find a specific point is from a group comprising: a display for a user to view point information, a RFID location tag and an associated reader, a GPS coordinate and an associated GPS receiver, a barcode location tag and an associated reader, and a combination of two or more of these. The programmed logic further interprets reporting characteristic results using an inference engine to derive logical observations and actions a user may recommend based on the reporting characteristic results.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

FIGS. 5A-5D are screen shots of the display for the unit shown in FIG. 1 showing a route and displayed oil properties;

DETAILED DESCRIPTION OF THE INVENTION

Figure 1:
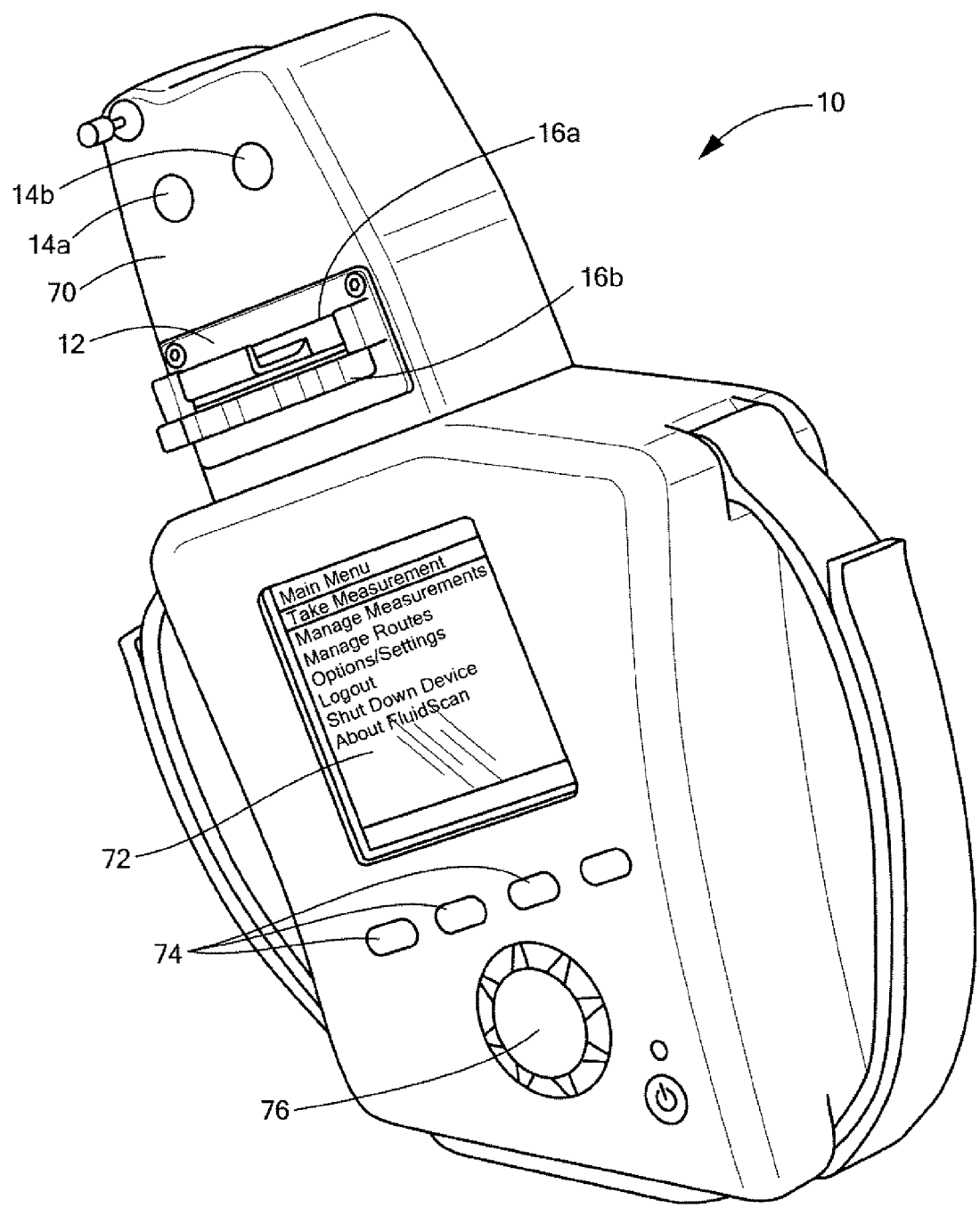
FIG. 1 is a schematic three dimensional front view showing one example of a hand held, portable route based analysis unit in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 depicts an example of a hand held, portable processor based route based oil analysis system 10 with flip top style oil sample cell assembly 12. See U.S. Pat. No. 8,384,895 incorporated herein by this reference. Magnets 14a and 14b releasably retain plate 16a on housing 70 when the sample cell is open for loading with an oil sample. Other sample cells are known to those skilled in the art. Transmission type, reflectance, ATR, DRIFT, and other sample cell technologies may be used.

There is output display screen 72 and input devices such as button 74 scroll wheel 76 used to make selections amongst menu driven options displayed on screen 72 generated via software operating on a processing subsystem in unit 10.

Within unit housing 70 is an infrared spectrometer subsystem configured to produce a spectrum for oil introduced into sample cell assembly 12 between windowed plates 16a and 16b. In one example, such an infrared spectrometer subsystem includes infrared source 62, FIG. 2 which emits radiation 63 passing through window 30a in plate 16a, oil sample 60, and window 30b in plate 16b. Thereafter the radiation proceeds to an analyzer 64 typically including a detector apparatus all of which may be engineered in accordance with U.S. Pat. No. 6,289,149; and U.S. Pat. No. 5,856,870; and/or U.S. patent application Ser. No. 11/347,482. The infrared spectrometer subsystem analyzer preferably outputs an infrared spectrum for the oil sample under analysis. Other infrared spectrometer subsystems, however, may be used or even other analyzers can be used based on spectrums of electromagnetic energy such as visible light, ultraviolet light, and the like. Also, substances other than oil can be analyzed such as fuel, water, and the like.

Figure 3:
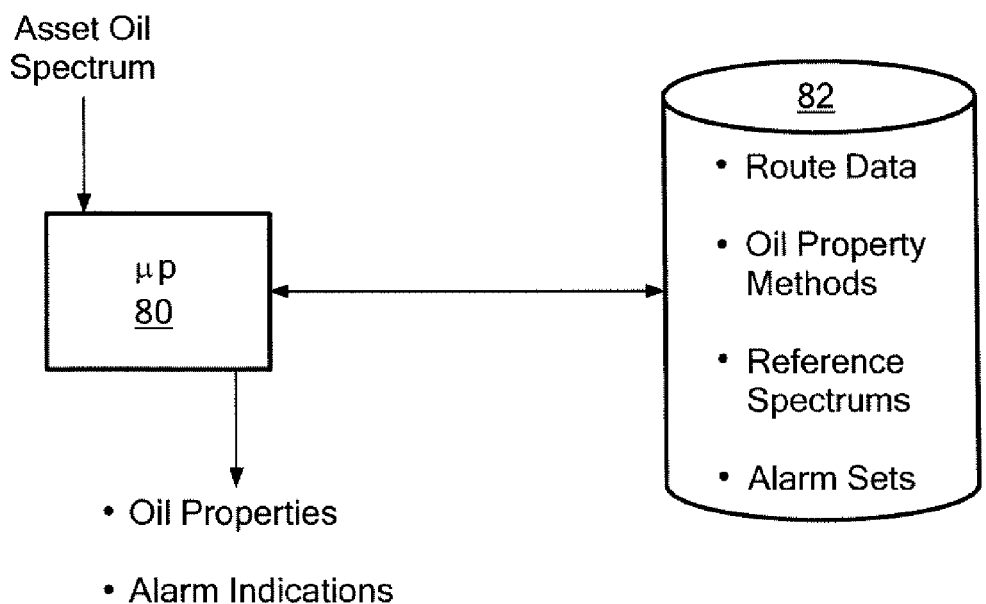
FIG. 3 is a block diagram showing the primary components associated with an example of a processing subsystem of the analysis unit depicted in FIG. 1.

This spectrum is then analyzed using programs operating on processor 80, FIG. 3 which computes and displays various oil properties and alarm indications on output screen 72, FIG. 1. Analysis methods so programmed vary based on the type of substance being analyzed (e.g., its chemistry and the like).

Figure 2:
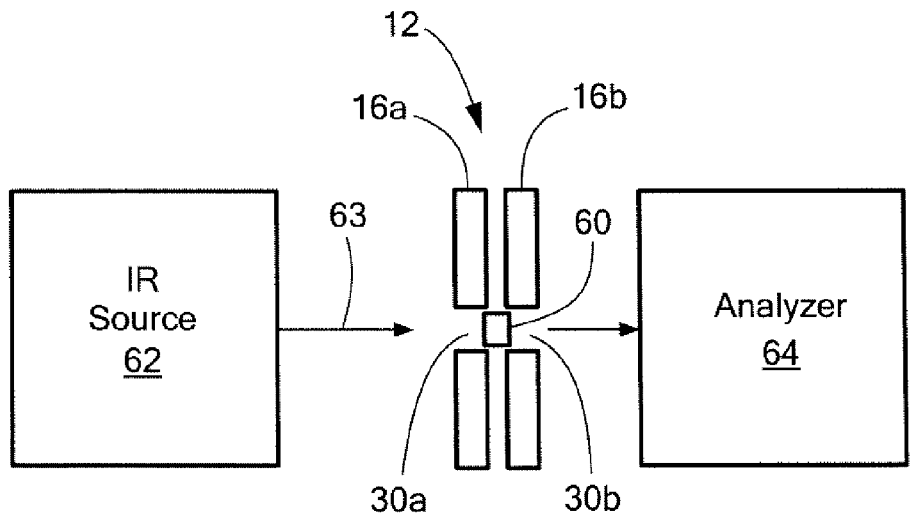
FIG. 2 is a schematic block diagram showing the primary components associated with an example of an infrared spectrometer subsystem for the unit shown in FIG. 1.

Processor 80 may be a microcontroller, field programmable gate array, CPU, GPU, application specific integrated circuit, processor, and/or co-processor which may be combined with analyzer 64, FIG. 2 or may include distributed systems (e.g., a separate laptop or PC) or the like.

Housing 70 may also contain one or more memory chips or devices such as read only memory or random access memory storing data, information, and calculations and data equations collectively shown as database 82, FIG. 3, containing (via uploads, for example) route data, oil property methods for different assets on the route, and reference spectrums along with alarm limits specific to different types of assets. In one example, one inspection point along the route is a machine with a gear box filled with oil. Data base 82 contains the location of that asset, instructions to sample the gear box oil, the type of oil (e.g., its chemistry, an identifier, its properties, additives used in the oil, a reference spectrum for the oil, and the like), oil property analysis methods (e.g., calculations, specific weights to be used in convolution functions, wave length regions to be analyzed, and the like). The alarm limits for certain oil properties based on the machine and/or its oil, and the like. Processor 80 locates and loads this data and information, in order to perform an analysis of the oil. The processing subsystem 80 displays on the output (e.g., screen 72, FIG. 1) a route including assets with oil to be inspected using the route data stored in database 82. See U.S. Pat. Nos. 7,454,050 and 5,637,871 incorporated herein by this reference. Thus, the processing subsystem is programmed or otherwise configured to display route data, step 90, FIG. 4.

In one route based example, the user may read text (and/or view graphical information such as maps, plant layouts, and/or floor plans or the like including pictures or other depictions of various assets (e.g., equipment)) on screen 72, FIG. 1 instructing the user to proceed, for example, to a gas turbine engine at a specific location (inspection point) on a factory floor and sump the oil of the gas turbine engine. See FIGS. 5A-5B. The user loads this oil into sample cell 12 and then uses an input button 74 and/or scroll wheel 76 to initiate the analysis, step 92, FIG. 4.

Analyzer 64, FIG. 2, then, in response, produces a spectrum of this oil as discussed above and processor 80, FIG. 2, from database 82, determines the type of oil (oil ID) used in each asset using the route data, asset information, input oil types, and the like. Based on the type of oil, and its identification, and/or its chemistry and/or the machine using the oil (collectively, type of oil), the appropriate oil property method(s) and reference spectrum(s) are located in database 82, FIG. 3. See steps 94-100, FIG. 4.

These methods are used in the computations to analyze the spectrum provided by the analyzer to the processor to output oil properties such as water content, acidity, soot content, additive type and content, oxidation levels, and the like. The presence of incorrectly added substances can be detected and reported, step 100, FIG. 4. See FIG. 5C.

In another example, an inspector proceeds to an asset and uses a bar code reader to input to the system the asset's oil type (e.g., chemistry) asset type, analysis methods, alarm limits, and the like based on a bar code label on or near the asset.

As noted previously, different oils require different analysis methods, calculations, spectroscopic techniques and even different wavelength region integrations and convolution function weights to arrive at correct acidity estimates and the like using the differences between the detected oil spectrum and the reference spectrum. Also, different assets have different alarm sets (threshold values, out of limit levels) which are stored in database 82, FIG. 3 for each machine. Alarm limits, for example, can be functions of the oil type, the machine type and/or age, or combinations of such data.

For the gas turbine example, processor 80 returns and runs the appropriate oil property methods based on the known oil type in the gas turbine engine, returns the reference spectrum for that oil, and returns the alarm set(s) for the particular gas turbine engine being inspected. See steps 96-100, FIG. 4.

Figures 5C, 5D:
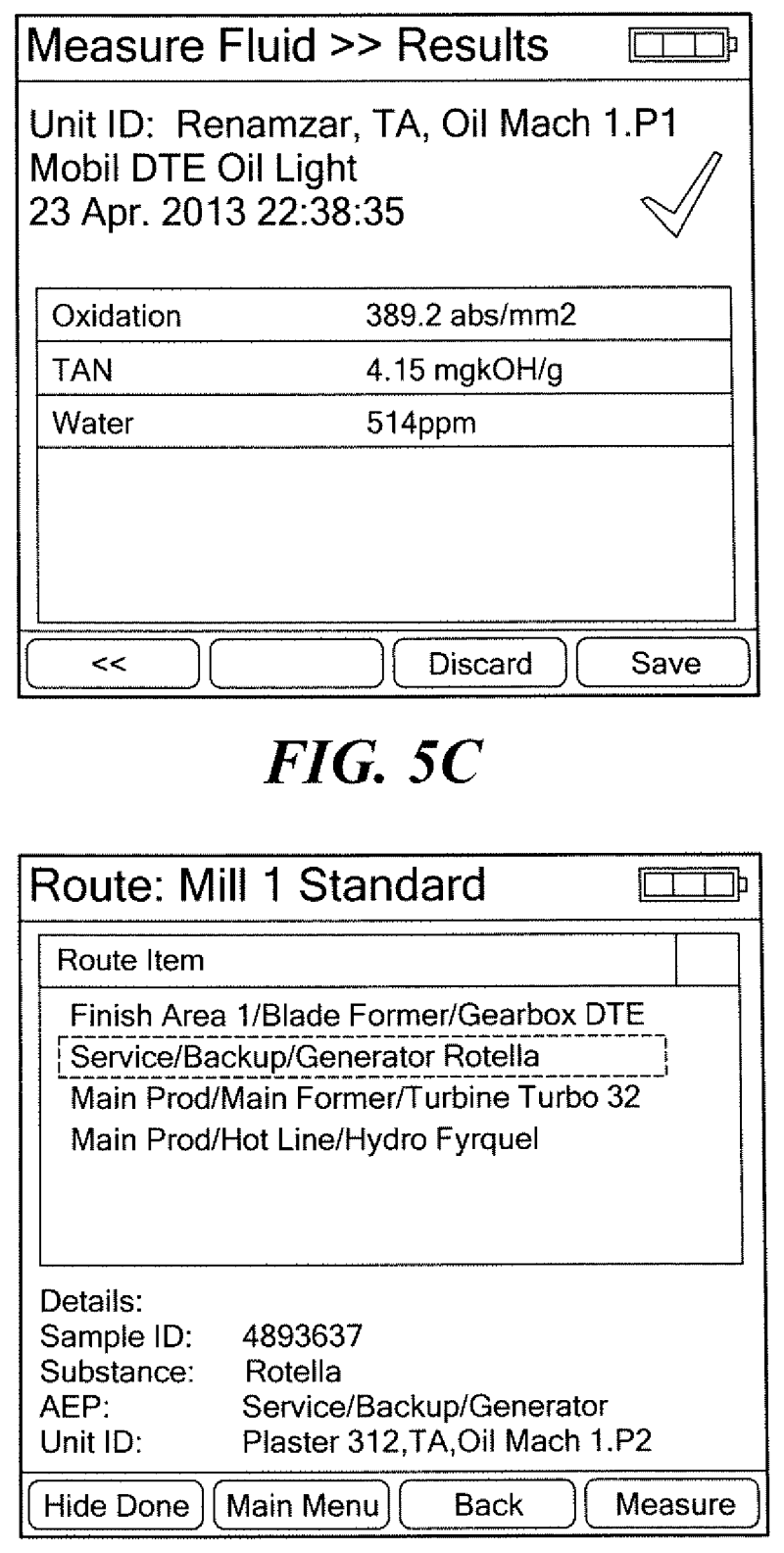

In one example, another inspection point is a diesel generator. FIG. 5D shows a second inspection point in the route of FIG. 5A. Processor 80 returns and runs the appropriate oil property methods based on the known oil type in the diesel generator, returns the reference spectrum for that specific diesel generator oil, and returns the alarm set(s) for the particular diesel generator being inspected.

Typically, the alarm set(s) for the gas turbine engine will be quite different than the alarm set(s) for the diesel generator. The allowed water content and acidity, for example, may be relaxed in a diesel generator compared to a gas turbine engine. Also, using the appropriate oil type and oil property methods to analyze the infrared spectrum for that oil produced by the infrared spectrum subsystem enables the calculation of a total acid and/or saponification number and a total base number. For the oil used in the diesel generator, the total acid number is not applicable while for the oil used in the gas turbine, the total base number is not applicable.

In analyzing the spectrums for the gas turbine engine oil and the diesel generator oil, integrations may occur over different wavelengths ranges (e.g., 2.5-5 µm for the gas turbine and 5-11 µm for the diesel generator) and the weighted convolution functions used to compute various properties based on the above described integrations may have different weighting factors.

Figure 4:
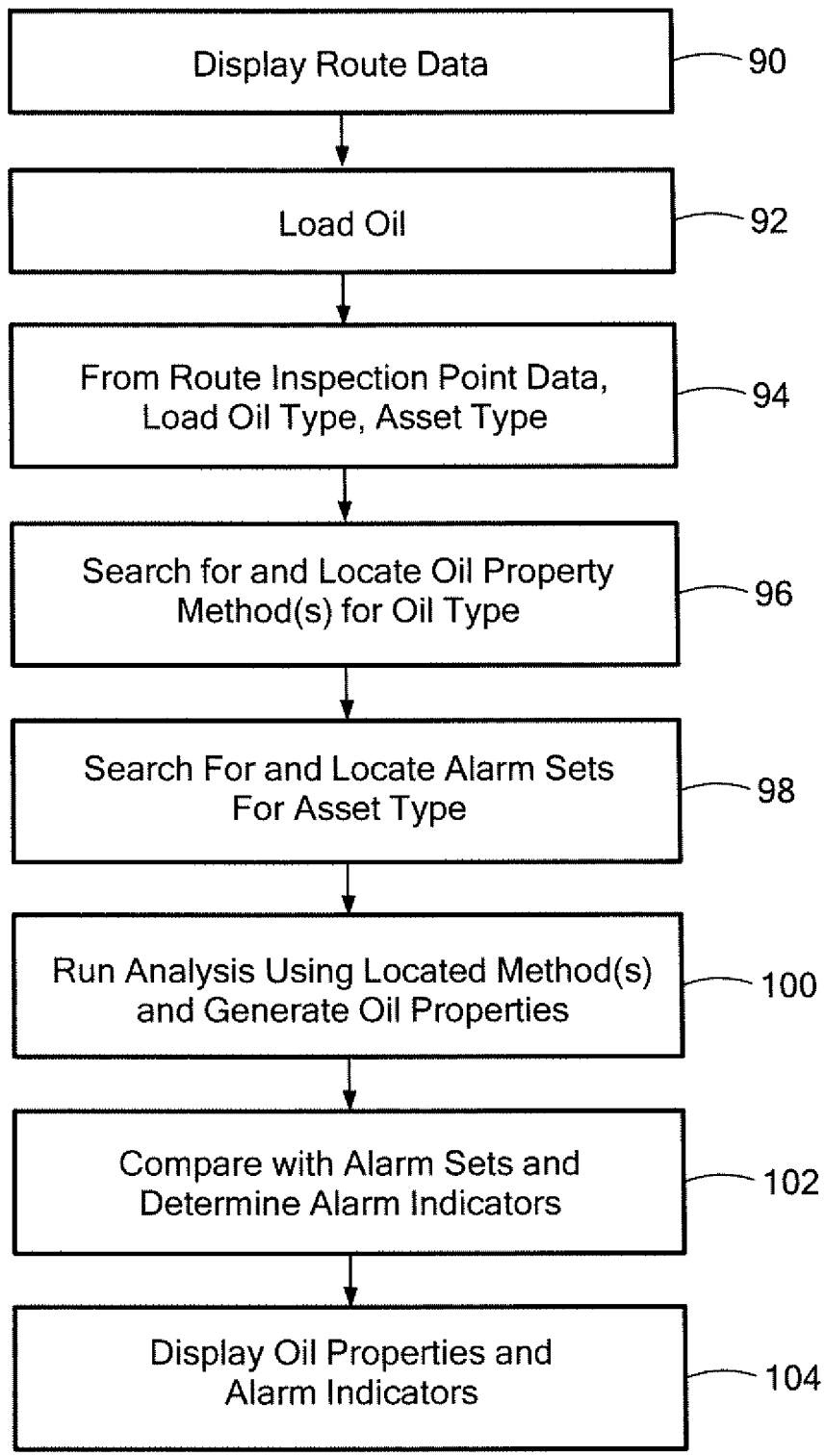
FIG. 4 is a flow chart depicting the primary steps associated with a route based analysis method in accordance with the invention and also depicting the primary steps associated with the computer software operating on the processor shown in FIG. 3.

Processor 80 thus displays the appropriate oil properties on display 72, FIG. 1 along with any alarm indications, step 104, FIG. 4. For example, if the percent water is too high, the value of the computed water content may be displayed in red or via a flashing number or the like. Recommendations may also be displayed based on the alarm indications including instructions to change the oil, add a certain additive, or the like.

The processing subsystem also usually generates and stores reports for each asset noting the date and time of the inspection, the inspection results, actions recommended and/or taken, trend analysis based on previous reports, and the like. Such requests may be stored in database 82, FIG. 3 and/or uploaded to a master computer subsystem using wired or wireless (e.g., Wi-Fi) connections.

In other examples, the inspection device tests viscosity (see Published U.S. application No. U.S. 2012/0180553 incorporated herein by this reference). The inspection system could also include particle counting/imaging subsystems, and the like. Other equipment using oil includes compressors, transmissions, and the like.

In industrial plants today, it is preferable for machinery health inspections to be carried out by personnel who follow a pre-defined inspection route. This "walking the beat" approach provides an extremely effective tool for performing efficient machinery analysis using a variety of tools. Such an approach has the advantages of on-the-spot, real-time inspection and data aggregation along with the advantageous economics in many situations where it is not cost-effective to permanently install inspection equipment on each asset.

Determining quantitative lubricant properties has to this point not been able to meet the tempo of operations of these pre-defined route health inspections. Analysis should be performed in seconds at each survey point, to a minute or two at the latest. With the advent of handheld unit 10, FIG. 1, it is possible to read critical, quantitative oil parameters within 1-2 minutes for the entire process right at the sampling point of the machinery. In one example, the route-based analysis would proceed as follows.

A maintenance server is configured to generate oil analysis routes based on a set of analysis rules. These rules may be time-based, previous condition-based, or specified by the maintenance engineer. The route could include: an asset sequence order, asset identification, and reference oil information that is needed (such as oil name, type, property limits, etc.). See step 94, FIG. 4.

The generated route is synched between the maintenance server and the device which will carry out the route-based analysis. This can be accomplished in a number of ways, including a straight database synch, a file download/transfer, or a bar code list which could serve the dual-purpose of a sample bottle label. For a set of recurring routes, a binder of 8½×11 sheets could be constructed that could be pulled and scanned in whenever that route is indicated. Sample labels afford a benefit of potentially including other data independently collected from lab or other onsite test instruments into this same sample record. Yet another way to accomplish this would be for the customer to print and laminate point labels to be attached to every sample point. Then when the customer walks the route he/she might scan the barcode and thereby build a route.

With the handheld machine loaded with and displaying the route, analyses are performed on each asset. The handheld machine operates in a self-guiding fashion so that the user, when finished with the analysis of a given asset, is presented with the next asset's information. See step 90, FIG. 4. This may include GPS coordinates of the asset, a picture of the physical asset, serial number, or simple instructions on where to locate the asset. The handheld machine contains all the calculation tools necessary to perform the analysis in database 80, FIG. 3.

The results of each asset scan are stored in the database of the handheld device. The operator views these results once they are produced. They can include alarm limits imported from the maintenance server so that the operator can see immediately if the machine is "in-spec" or out-of-spec according to the analysis. If out-of-spec, additional instructions may be offered to the operator, such as to collect a bottle of sample for further analysis.

When the route is complete, the handheld device is again synched with the maintenance server. The maintenance engineer can then peruse this data and use the server's analysis tools to determine further action regarding the assets on the route.

With this type of system in hand, route-based oil analysis is now a valuable tool for a large facility that already may be performing route-based machinery health monitoring. With the natural flow of a route-based system, it shows decision-makers how oil analysis can literally tit into the context of their other tools. It also provides a convenient and practical way to perform oil analysis with minimum or no paperwork. Further, as we look to the future, and as at-line, in-line and on-line tools emerge for oil analysis in the way they have for vibration monitoring, we can see a similar path forward for these two probes of machinery health. By using a route-based oil analysis, one can plan coverage a whole range of assets based on economic and ROI considerations. Dedicated in-line and on-line analyzers which have the same capabilities as the handheld at-line tools may be used where appropriate, with that data stream tied together with the route-based system into the maintenance server and overall system. Architectures which are more practical with the status of today's instrumentation, which primarily involve less capable in-line and on-line oil analysis instruments relative to the at-line or laboratory measurement, can also be considered but the effectiveness of such a heterogeneous system can be challenging for certain applications, especially those where near lab-grade quantitative results are a necessity.

At the same time, it is clear that oil analysis and other probes of machinery health such as vibration and thermography have fundamental differences that must be carefully considered when planning how and when to forecast using emerging oil analysis tools. As oil analysis is inherently a physical and chemical investigation of the oil including base and additives and contaminants and wear debris, it provides significant and different challenges from vibration or thermography, both of which at their core use information arising directly from the machinery itself. The chemical information must be extracted from the oil, which can then be used to make assessments of the health of machinery, the type and extent of system contamination, and the functional condition of oil. Orders of magnitude advances in the speed, size and weight of quantitative oil analysis tools indicate that realizing such advances as a route-based oil analysis paradigm are now possible.

Preferred embodiments of the present invention typically comprise a structured database 80. FIG. 3, route information associated with that database, a user preferred inspection route, a transfer of route with route information into a sensory system, a use of the route information during data collection and in-field analysis, and an uploading of measurements and findings to update the structured database.

Figure 6:
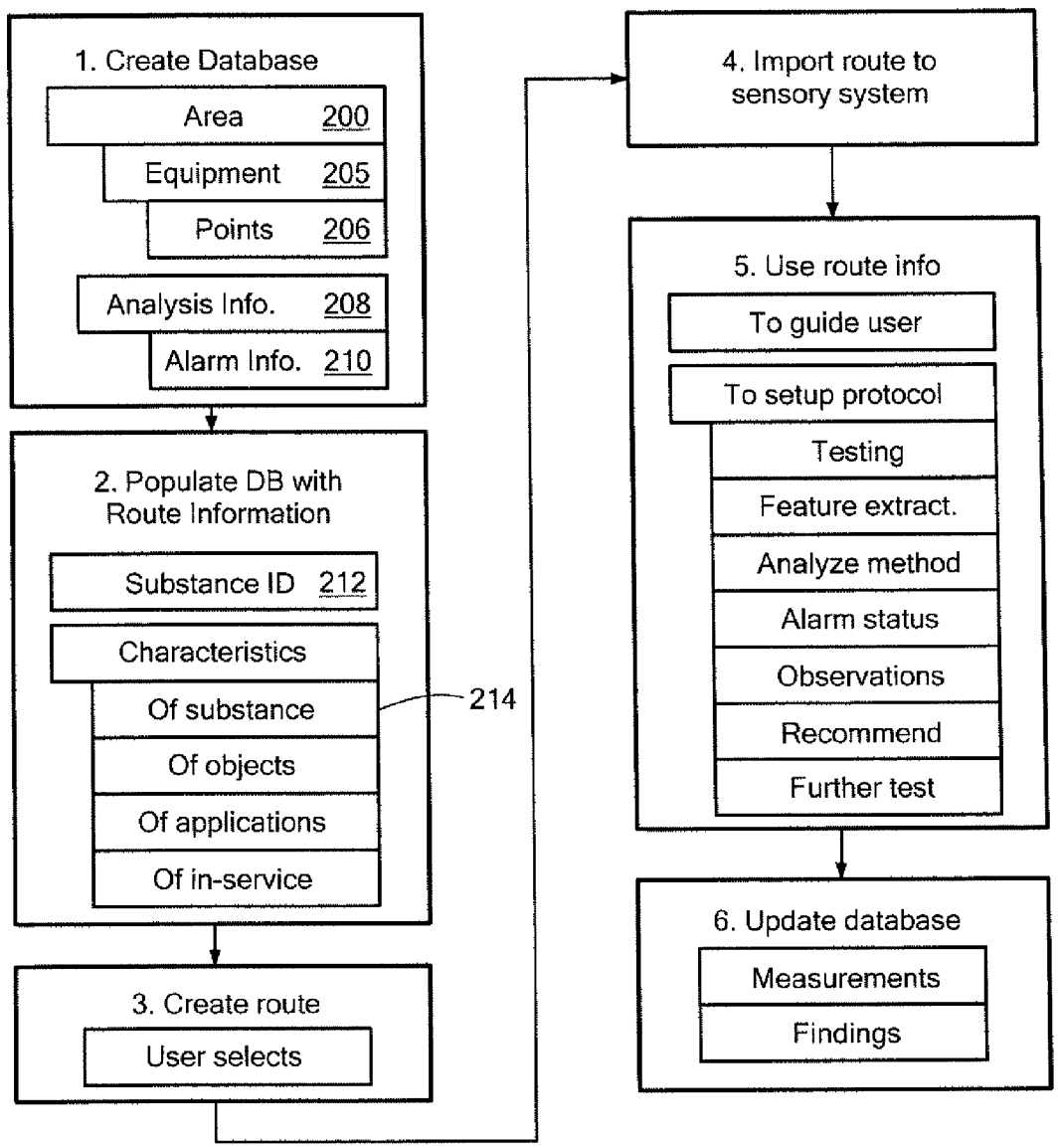
FIG. 6 shows the primary steps associated with populating a structured database as shown in FIG. 3.

As shown in FIG. 6, a structured database may comprise a hierarchical equipment database which is typically displayed in a multiple level tree structure wherein, for example, a top hierarchy level is an area or fleet or machine train or wing or some such designation. A database may include multiple areas 200, FIG. 6. Each area then includes one or more pieces of equipment 205 or vehicles or machines or aircraft or some such designation. In turn each equipment item includes one or more points 206 or measurement locations or sample ports.

The structured database typically includes analysis information 208 such as analysis parameter sets, as well as detailed information regarding types and units and setups and methods associated with parameters. Note that as used herein the terms parameter and property are preferably synonymous with measure and are not limited to parametric or normal statistical distribution. In fact some parameters referred to herein are causal and may not be normally distributed.

The structured database also typically includes alarm limit information 210 for at least a portion of the analysis parameters, wherein, an alarm limit is typically considered to be normal, low alert, high alert, low fault, or high fault condition based on a logical comparison of a parameter value with a defined set of alarm limits or thresholds. Alarm limits may be zero based or reference based or point based or another relevant baseline. Alarm limits may be based also on an absolute deviation from baseline or a percentage deviation. Alarm limits may be high or low compared with baseline or either high or low. Alarm limits may be based on an industry accepted or OEM recommended standard value, they may be based on rate of change, based on sorted cumulative distribution of a measured population, based statistical process control type calculations, or on another accepted approach. Still other alarm setting methods may be assigned to a structured database in accordance with the present invention as may be appropriate for an application.

Another aspect of the present invention is the population of a structured database with pertinent route information such as substance identification 212 of characteristics of substances, of objects, of applications, or of operations history for in-service applications, 214.

One aspect of the present invention is the storage of relevant substance information in a structured database so that when a route is created from that database, the relevant substance information is systematically published to a sensory system used in route-based substance analysis. This electronic transfer of substance information (e.g., oil type) to an in-field analysis tool enables the sensory analysis device to deliver more repeatable or accurate analysis results and to return those results to the structured database without error.

A particularly practical and useful aspect of the present invention is the use of a substance information characteristic of substance identification or substance ID or type. A substance ID is a designation given to a group of one or more different substances which are tested using an identical test sequence, feature extraction technique, and analysis method.

Substance information relevant to an in-field selection of a test sequence, a feature extraction technique, and an analysis method may further include new oil specifications, properties, and other descriptive information about the substance, its compatibility with other materials, its frailties, its strengths, and experience based findings published by practitioners.

In addition to substance ID, route information relevant to the present invention may include characteristics of objects which are in contact with the substance such as seals or bearings or pressures or flow rates. For example a phosphate ester lubricant is likely to have deleterious effects if placed in intimate contact with Buna-n rubber elastomers and seal materials. This asset information is stored in database 80, FIG. 3. Programmed logic in a programmed sensory system may recognize route information about a material compatibility along with test results to produce an observation regarding possible incompatibility and a recommendation to the user that this be verified and inspected.

Route information further may comprise characteristics of an application and further of in-service history for an application. For example route information may report that an asset (application) is an engine for a first point in a route and another asset or application is a transmission for the second point in a route. For this example the sensory system may be prompted to setup and test for engine oil analysis parameters in a first test and for gearbox or power transmission oil analysis parameters for the second test during a route-based oil analysis sequence. In this example, logic embedded into the sensory system can be used to check for possible misapplication of fluid where a wrong oil is in the application or for switched sample order where the first sample tested was in reality the transmission and the second was in reality the engine oil. Based on expected or historical values, programmed logic can be used to flag an observation regarding potentially misapplied oil or transposed measurements, thereby enabling an in-field user to immediately verify and then make accurate and validated recommendations.

Route-information characteristics regarding in-service status or operational history of an application may be transferred to the sensory system, thereby enabling the sensory system to display last measured values for each route point, to display or calculate rate of change for parameter values and to report alarm conditions. For example when a parameter is setup within an alarm limit set in the structured database it is useful to pass the alarm threshold values along with substance information to the sensory system so that the in-field user will immediately know how the next measurement taken compares with these thresholds.

In FIG. 6, step 3 involves user creation of a route. This may be accomplished in several different ways. For a first example a user may have predefined all the sample points in a database for scheduled sampling and analysis. In this example the user may query the database for a list of all samples past due or soon due for sampling and analysis. The structured database software may be structured to facilitate proximity association of these sample points such as a graphical display of the points on a floor plan to assist the user with a numbering sequence for walking through the route. For a second example, a user may construct a route by stepping through an equipment database and adding one sample per point to be tested. In this example as samples are added a batch list or route list is created with samples in the order in which they have been selected. Other manual or automated schemes for creating a logical route for walking the route are apparent to those skilled in the art.

In FIG. 6, step 4 the user imports route information into the sensory system. This may be done in any one of many different ways. Here are several of many examples: wired transfer using LAN or WAN or USB file transfer or RS232 or RS485; wireless transfer using Wi-Fi or Bluetooth or IrDA or barcode or RFID. One preferred embodiments of the present invention comprise using 2D barcode scans from sample labels or point labels printed using Emerson's OilView™ LIMS software. Another preferred embodiment of the present invention uses USB memory file transfer. A third preferred embodiment of the present invention uses Bluetooth or Wi-Fi file synchronization wherein the structured database and the sensory system synchronize route file transfer and results file (also called generic file) upload either on demand or more automatically.

In FIG. 6, step 5, a sensory system uses route information to guide a user through an inspection route and to select or setup certain protocols for testing, feature extraction, analysis method, alarm status information, observations, recommendations, and further testing.

The sensory system is typically enabled in the handheld device of FIG. 1 such as Spectro, Inc. "Q1100 FluidScan" product for example, wherein the device comprises a programmable platform supporting a sensor (the IR spectrometer) for achieving sensory contact resulting in an analysis to ascertain relevant information about a substance of interest. In the example of the Q1000 device is handheld, with a user interface display and joystick selector. This device is factory programmed and is further programmable using USB communications port and using joy-stick selector user input selections. Furthermore the Q1000 device, a flip-top-sample test cell is designed to accept a drop of test substance on one window of the flip top cell which is then slipped into position for transmission infrared spectroscopic examination of the substance. A second example of a sensory system is a device similar to Q1100 FluidScan which uses an attenuated total reflectance (ATR) type infrared analysis technique. A further example of a sensory device which may be incorporated into a portable sensory system is a dielectric tester or other electrical impedance tester such as the Test 1 or the Test 2 sensors in the Spectro 5200. A further example of a sensory device which may be incorporated into a portable sensory system is a ferrous density sensor such as Test 2 in the Spectro 5200, the Spectro Q200, GasTops'

MetalScan sensor, or Parker Kittiwake's PQ analyzer. Yet another example of a sensor technology suitable for incorporation into a sensing system of the present invention is the X-Ray fluorescence sensor from the Spectro Q5800 device.

As depicted in FIG. 6, step 5, one aspect of the present invention is the use of route information to affect and enable use of the sensory system in walk around transportable inspection of points along the route. In accordance with the present invention, a route information is used to assist the user (a user is an inspector or analyst or mechanic or technician or operator or engineer, one who uses the sensory system in route-based data collection to interrogated a substance of interest for relevant information). For example when route information includes text or graphic information related to recognizing a location for a measurement point or sample port, the sensing system can be programmed to present this user readable information so the user is synchronized with the instrument as testing and analysis is performed.

Furthermore route information to the sensory system serves as programmable logic. The sensory system is originally programmed typically by a factory or agent of the manufacturer to perform in general testing functions. These functions generally require numerous user selections and setups for a test in order to assure proper tests are conducted appropriate to the situation and substances. According to the present invention, additional programmed logic is specifically programmed into the sensory system to recognize and use relevant route information. Route information such as substance ID and characteristics of objects and characteristics of applications and characteristics of in-service operations are interpreted by this additional programmed logic to enable the sensory system to achieve greater repeatability and accuracy by effectively eliminating human error and automatically selecting the procedural steps such as the following: testing setup and testing sequence appropriate to the substance and application, feature extraction from data produced during tests, analysis methods for analyzing and comparing values representative of these extracted features, alarm status values, logical observations, logical recommendations, and logical further testing and validation.

Feature extraction involves analysis of data from a sensor by one or more transformations of at least a portion of thereof into a form in which one or more identifiable elements or features may be qualitatively or quantitatively measured, assessed, or otherwise evaluated.

Feature extraction may be explained using a examples from infrared spectroscopy typically produces a spectrum of energy output from Fourier transform or from a diffraction grating or from another technique. After that first transformation the resulting spectrum is further analyzed to extract features. Analysis may comprise subtracting or otherwise comparing the test spectrum with a baseline or reference spectrum. Further analysis then typically involves identifying peaks and areas and inflections and other characteristics identifiable in these spectral data sets which are commonly represented in a form of amplitude vs. wave number, although other accepted approaches are be used. Particular substances produce infrared absorption peaks with greater or lesser magnitudes than other substances. Therefore it may be important to know what features are expected for a normal, as new, spectra, compared with an in-service oil spectrum which may have further species such as carboxylic acids or water or glycol or soot. It may also be important to not make a false alert for soot in a substance that comes from a machine not capable of producing soot. These are just a few of many exemplary cases transferring substance ID to an in-field spectrometer.

For further examples of feature extraction, flow through induction sensors such are capable of detecting metallic particles by their back EMF signature. Feature extraction for such a signal may involve analyzing the wave form to distinguish rate of change, direction of change and peak amplitude in order. These characteristic features may be assignable to particle substance, such as ferrous vs. nonferrous, or to particle size, such as >100 microns or >150 microns. Other ferrous density techniques mentioned earlier also have distinctive data signatures from which feature may be extracted to distinguish particulate morphology, concentration, size, and more. Particles such as these are typically not contained in the new substance and instead are a result of degradation of one component or another. Features which may be indicative of a morphology or a material which may be confused without route information can be better interpreted using an in-field sensory system by carrying such route information into the field during a route inspection.

For yet further examples of feature extraction one may consider use of a sensory system comprising an X-Ray fluorescence detector which well known for distinguishing relative proportions of metals within an alloy. By combining route information with data produced by an XRF detector, one may translate proportions into more meaningful information more representative of a total mass of an elemental material or a percentage or a parts per million or an index or code value. Typically this involves setting up a repeatable testing situation wherein under repeatable conditions, one may extract the more meaningful information, and those conditions may be associated with one or more aspects of route information because the a similar measurement is made under similar conditions at that point each time the route inspection is exercised. These several examples are not intended to demonstrate an exhaustive list of how route information and feature extraction can be made useable in route-based substance analysis. Instead they are provided to demonstrate the variety of ways in which route information and sensory system combine to produce effective and meaningful measurement results.

The sensory system preferably comprises a transportable system configuration; at least one sensor for making sensory contact with a substance in the field; at least one display or other mechanism for transforming information to the user from the sensory system; at least one user input mechanism for transferring information from the user to the sensory system; at least one data port capable of data input and at least one data port capable of data output; at least one central processing unit (CPU) operationally connected to a memory to a data input/output port and to the at least one sensor, the at least one mechanism, and the at least one user input mechanism; at least one program loaded into the at least one CPU to operate the survey system for measuring a substance; and at least one route data set having specific route information for interpretation by the at least one program.

One skilled in the art will understand that it is not necessary for all these elements listed to be transported in order for the sensory system to be transportable. For example in certain embodiments it may be suitable for one or more sensors to be imbedded or mounted in the field such that when an operator connects up to that sensor, whether by direct physical connection or by remote wireless connection. This is particularly relevant when a sensor must be installed in a difficult to access or dangerous location. For another example it is conceivable that with virtual operation or thin client that a handheld system may operate using remote computational assistance.

Power must be provided to the transportable sensory system. For most situations this requires a battery or energy harvesting source of electrical power. For most situations it is impractical to use line power because of the remoteness and inaccessibility of line power for many in-field sites.

In FIG. 6, step 6, all pertinent measurements and finding from the route may be exported from the sensory system back into the structured database using an accepted protocol such as Emerson's generic.doc format.

Those who practice walk around inspections and substance analysis will recognize benefits of time saved and errors eliminated by allowing programmable computerized devices to perform repetitive functions, identifying characteristics of substances and in-field applications. A database wizard like that described in U.S. Pat. No. 6,192,325 greatly reduces errors in creating structured databases. In similar manner, the present invention further speeds up process while eliminating human errors by automatically carrying route information which is critical to the testing and analyses processes into the field.

An alternate embodiment of the present invention involves substituting a point recognition for a route instruction when using to avoid or reduce human error introduced during oil sampling and analysis through the use of programmed logic to correctly identify a testing technique and an out-of-limit level and rely on the human inspector to correctly identify the measurement point in the field. For example, an inspector may use a reader to interpret a machine readable identification such as a bar code or an RFID tag located in a vicinity of an oil compartment, an equipment, or a sampling point. In this embodiment an inspection may follow any route and still be assured of correct location identification for a point or equipment or compartment. The result is that programmed logic is able to use that association with at least a portion of a structured database having similar information to the route information to look substance ID, feature extraction, test method, out-of-spec alarm limits, and much more.

Figure 7:
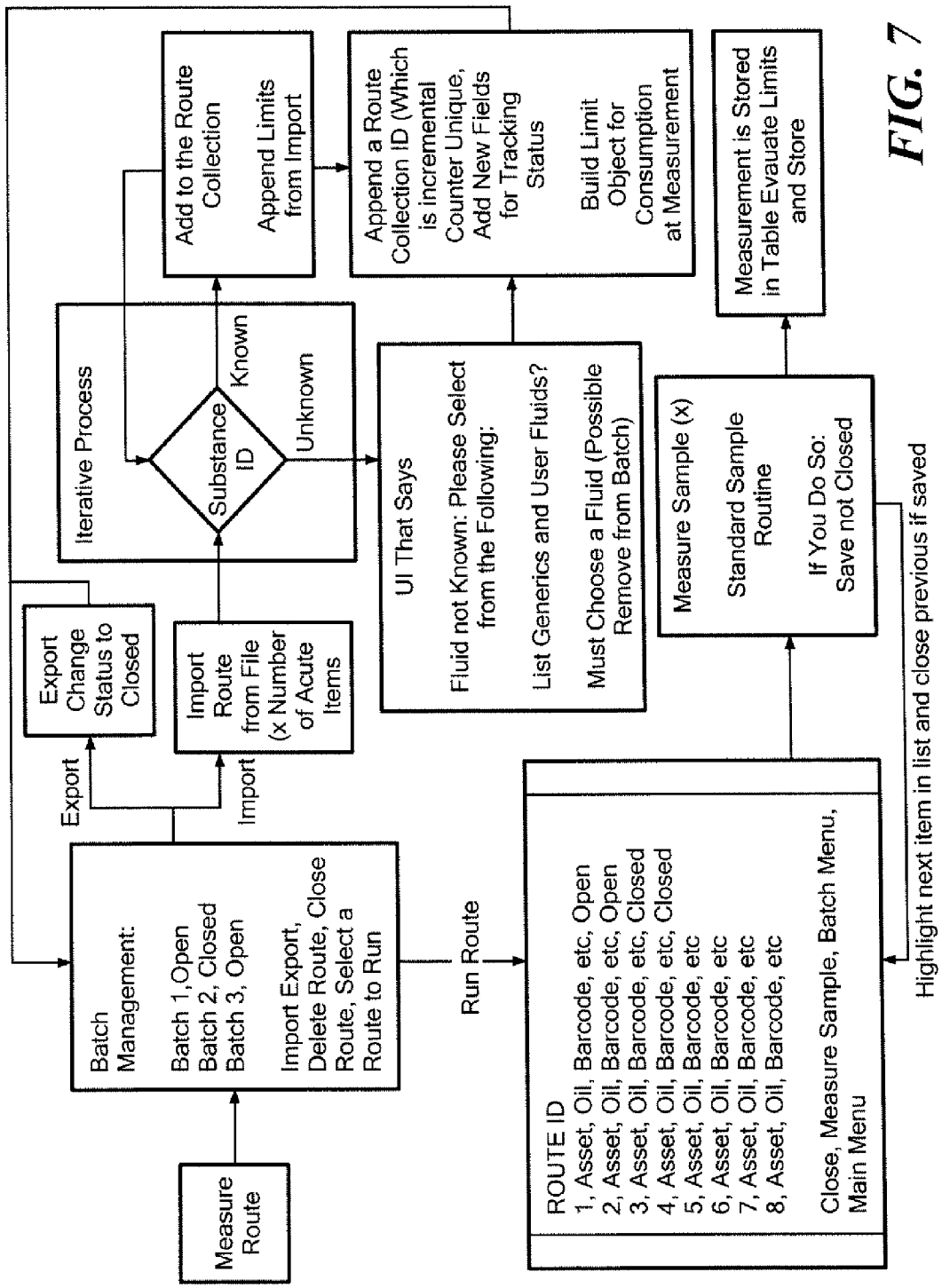
FIG. 7 is another flow chart depicting the several steps associated with the programming of the processor shown in FIG. 3.

The interface between the master database software and the IR spectrometer instrumentation is described as follows where FIG. 7 provides an overview of the workflow of the system.

Figure 8:
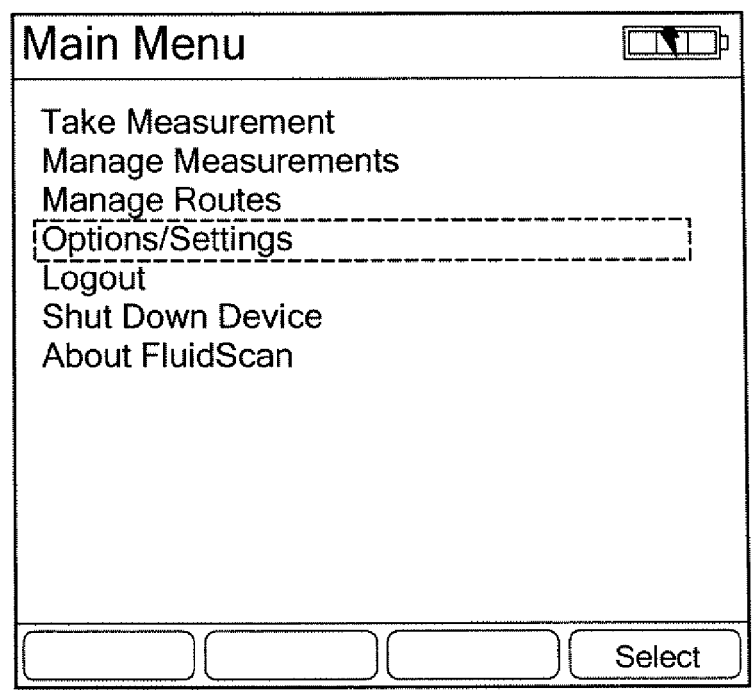
FIG. 8 is a depiction of the main menu generated by the programming associated with the processor of FIG. 3 displayed on the display screen of the system shown in FIG. 1.

Task: Create New "Route Management" Screen
Description:
Clicking on the Manage Routes item in the main menu, FIG. 8 will bring the user to the "Batch Management" screen.

This screen will present the user with a list of all batches still in the system along with their status.

The first row will be selected and highlighted by default.

Soft Buttons (SB) at the bottom of screen will change depending on which row is currently selected in the list.

Status Options:

| Status | Description | Soft Buttons (if row is selected) | |
|---|---|---|---|
| New | Have not started route | SB1: Run Route SB2: SB3: SB4: Main Menu | Brings up the Run Route Screen Return to Main Menu |
| Open | Started Route | SB1: Run Route SB2: SB3: SB4: Main Menu | Brings up the Run Route Screen Return to Main Menu |
| Closed | Route has been manually closed by user (may not have completed all samples) | SB1: Open Route SB2: Export Route SB3: Delete Route SB4: Main Menu | Changes status back to Open Brings up Export Screen Confirms then Deletes Route Return to Main Menu |
| Exported | Route has been exported (at least once). Flag resets if route is reopened. | SB1: Open Route SB2: Re-Export Route SB3: Delete Route SB4: Main Menu | Changes status back to Open Brings up Export Screen Confilms then Deletes Route Return to Main Menu |
| <No row selected> | No row is currently selected | SB1: SB2: SB3: SB4: Main Menu | Return to Main Menu |

List Columns:

| Column Header | Value | Comments |
|---|---|---|
| Status | Integer 0 = New 1 = Open 2 = Closed 3 = Exported | |
| Batch | Date/Time Stamp in Sample | All samples within a batch will have the same date/time stamp in each record. We will use this as the "Name" of the Batch. Internally we will generate a unique BatchID. |

Task: Create New "Run Route" Screen
Description:
The "Run Route" screen provides a list of all samples to be done for this route.
Task: Create New "Import Route" Mechanism
Master Database will provide the capability to export sample batch information by exporting the necessary data into a CSV (comma separated values) file.
The file will be written to a USB stick so it can be transferred over to the mobile device.
Each row in the file represents one sample request and is terminated with a CRLF. The samples will be ordered in the device based on the order in the file. If there is no value for a given field, there should still be a comma to maintain the position of the data.
Minimum Required Fields per Row:
Handheld, portable route based analysis unit will require at a minimum:
    Date
    SubstanceID If there is no associated SubstanceID, Master Database will pass ID=0. In this case, the device will use the "Generic" oil with minimal IR properties
At least one of the following
ID
UnitID
Area, Equipment & Point
Field Definitions

| Pos | Field | Description | Data Format |
|---|---|---|---|
| 1 | ID | The Sample ID | integer |
| 2 | Date | Sample Date | MM/DD/YYYY |
| 3 | SubstanceID | The Unique Spectro Substance ID. This value allows us to identify the specific oil that is being tested. | integer |
| 4 | SubstanceName | The Master Database name of the oil. | string |
| 5 | Area | Top level descriptor of the sampling point | string |
| 6 | Equipment | Name of equipment that sample is from | string |
| 7 | Point | Sampling Point | string |
| 8 | UnitID | User-provided ID to uniquely identify the sampling point | string |

Example Import File:
75090,10/3/2012 11:36:12 AM,201,"Anderol Royco 783", "A022 Tribology Area", "RVPUMP#1 Vane Pump#1(Coolant Leak)","OP1 Bottom drain off vacuum pump", "rvpump1"<CRLF>75092,10/3/2012 11:36:12 AM,201, "Mobil—Mobil Gear—634","A022 Tribology Area", "Oil Mach 2 Ferrous in Oil","P1 Oil sample point", "8215"<CRLF>75094,10/3/2012 11:36:12 AM,0,"","A022 Tribology Area", "Oil Mach 2 Ferrous in Oil","P3 New Point", ""<CRLF>
Object & Database:
New Objects:
  Route
  Members
    String: routeGUID
    String: routeName (from Date Field)
    Int: status
    List<RouteItem>: RouteItems
  RouteItem
  Members
    String: routeItemGUID
    Route: route
    Int: status (New, Skipped, Done)
    Int: sampleID (SampleID from Import)
    Int: substanceID (from Import)
    String: importedSubstanceName (from Import)
    String: area (from Import)
    String: equipment (from Import)
    String: point (from Import)
    String: unitID (from Import)
    Measurement: measurement
    Substance: substance
Step 1: Parse in the Route Import File
  Create Route instance
  Parse in first row
  Generate new GUID and set RouteGUID
  set RouteName using value from DateField
  set Status=New
  For each row
  Create RouteItem instance
    Generate GUID and set RouteItemGUID
    Set RouteGUID from Route instance
    Set Status=New
    Set additional fields in RouteItem from row data
    Add RouteItem to Route.RouteItems list
Step 2: Validate and Flesh Out Object Structure
  For each RouteItem in Route
    Validate SubstanceID
      If ID>0, retrieve Substance
        If Substance=null (no Substance found), process ResolveUnknownSubstanceID( )
        If Substance< >null, set routeItem.substance
      If SubstanceID=0, then ProcessGenericSubstance( )
Task: Create Alarm Limits
Master Database will provide alarm limits as part of the route import file. Each route record may contain one or more limit records (one per property). Not all properties require limits. Properties will be mapped between Master Database and Hand held, portable route based analysis unit using the internal Parameter ID. This is the same parameter that will be used when exporting the data out to Master Database.
The Hand held, portable route based analysis unit may use these limits for this single sample instance. It does not store the limits to be used in future samples.
Master Database has several different limit types and variations.
Master Database Limits
  Sample Point-based or Reference-based
  % or Absolute Values
  Upper Limits/Lower Limits and Both
For example: the most common limits will be for the following properties
TAN, TBN
  IMPORT: % variation from a given reference value
  CONVERT:
    Upper Limit=ReferencePoint+(ReferencePoint x %)
    Lower Limit=ReferencePoint−(ReferencePoint x %)
Water
  IMPORT: Absolute upper threshold
  CONVERT:
    Upper Limit=ReferencePoint
Visc
  IMPORT: Upper and lower absolute range
  CONVERT:
    Upper Limit=Upper ReferencePoint
    Lower Limit=Lower ReferencePoint
1.1.5 Export Results
The Hand held, portable route based analysis unit will generate an export file following the generic file format for Master Database data importing. Any information provided as part of the original route import will be provided back to the Master Database system though the export file.
Below is an example list of all the properties (parameters) that can be generated from the Hand held, portable route based analysis unit Properties

| Property Name | UOM | Master Database Keyword | Description |
|---|---|---|---|
| V40 | cSt | VISC40 | Visc at 40 degrees |
| Oxi | abs/mm2 | IROXIDAT | ASTM Oxidation |
| Nit | abs/mm2 | IRNITRAT | ASTM Nitration |
| Sul | abs/mm2 | IRSULFAT | ASTM Sulfation |
| TBN | mgKOH/g | TBN | TBN |
| TAN | mgKOH/g | TAN | TAN |
| Water | Ppm | WATERKF | Water |
| Gly | % vol | FS_GLYCOL | Glycol |
| AWAdd | % depleted | FS_AW | Additive depletion |
| AlienMin | % mineral | FS_AM | Alien Fluid mineral |
| AlienHyd | % hydro | FS_AH | Alien Fluid synthetic hydro |
| AlienTurb | % turbine | FS_AT | Alien Fluid turbine |
| BD1 | abs/mm2 | FS_BD1 | ASTM Turbo Breakdown I |
| BD2 | abs/mm2 | FS_BD2 | ASTM Turbo Breakdown II |
| AOx | % remain | FS_AOX | Turbo Antioxidant Depletion Status |
| FRW | abs/mm2 | FS_FRW | Free Water |
| Gly | % mass | FS_GLY | Total Glycerin in Biodiesel |
| Ffa | % mass | FS_FFA | % Free Fatty Acid in BD Feedstock |
| % BD | % vol | FS_BD | % Biodiesel in Diesel |
| Bub | Abs | FS_BUB | Bubbles in Oil |
| AWc | abs/mm2 | FS_AWC | ASTM Antiwear Components |
| WatA | abs/mm2 | FS_WAT | ASTM Water |
| GlyA | abs/mm2 | FS_GLYA | ASTM Glycol |
| Awa | abs/mm2 | FS_AWA | ASTM Antiwear Keyword |
| StA | Abs * 100 | FS_STA | ASTM Soot |
| Ar1 | % | FS_AR1 | Area I Check |
| Ar2 | % | FS_AR2 | Area II Check |
| Soot | % Wt | FS_SOOT | Soot |
| Disp | Ml | FPQ_D | Fluid Dispensed in ml |
| Part_4m | #/ml | FPQ_4M | Particles >4m |
| Al | ppm | XRF_AL | Aluminum |
| Ti | ppm | XRF_TI | Titanium |
| Cr | ppm | XRF_CR | Chromium |
| Ni | ppm | XRF_NI | Nickel |
| Cu | ppm | XRF_CU | Copper |
| Pb | ppm | XRF_PB | Lead |
| Ag | ppm | XRF_AG | Silver |
| Sn | ppm | XRF_SN | Tin |
| Mo | ppm | XRF_MO | Molybdenum |
| Si | ppm | XRF_SI | Silicon |
| Zn | ppm | XRF_Zn | Zinc |
| V | ppm | XRF_V | Vanadium |
| P | ppm | XRF_P | Phosphorous |
| Ca | ppm | XRF_Ca | Calcium |
| K | ppm | XRF_K | Potassium |
| Co | ppm | XRF_Co | Cobalt |
| Cd | ppm | XRF_Cd | Cadmium |
| Ba | ppm | XRF_Ba | Barium |
| Na | ppm | XRF_Na | Sodium |
| Fe | ppm | XRF_Fe | Iron |
| Sb | ppm | XRF_Sb | Antimony |
| Bi | ppm | XRF_Bi | Bismuth |
| As | ppm | XRF_As | Arsenic |
| In | ppm | XRF_In | Indium |
| Zr | ppm | XRF_Zr | Zirconium |
| Mn | ppm | XRF_Mn | Manganese |
| W | ppm | XRF_W | Tungsten |
| Rh | ppm | XRF_Rh | Rhodium |
| Nb | ppm | XRF_Nb | Niobium |
| Ce | ppm | XRF_Ce | Cerium |

-continued

| Property Name | UOM | | Description |
|---|---|---|---|
| Sr | ppm | XRF_Sr | Strontium |
| SampOrderSeq | n/a | SampOrderSeq | Sequence # |
| SampNum | n/a | SampNum | Sample # |
| SoftwareVer | n/a | SoftwareVer | LNF SW Version # |
| LNFNum | n/a | LNFNum | LNF S/N |
| OperatorID | n/a | OperatorID | Operator Making Meas |
| Notes | n/a | Notes | Notes |
| ConcentrationMult | n/a | ConcentrationMult | Fraction dilution |
| MDiamCum5 | #/ml | MDiamCum5 | #/ml >5 use max dia |
| MDiamCum10 | #/ml | MDiamCum10 | #/ml >10 use max dia |
| MDiamCum15 | #/ml | MDiamCum15 | #/ml >15 use max dia |
| MDiamCum20 | #/ml | MDiamCum20 | #/ml >20 use max dia |
| MDiamCum25 | #/ml | MDiamCum25 | #/ml >25 use max dia |
| MDiamCum50 | #/ml | MDiamCum50 | #/ml >50 use max dia |
| MDiamCum100 | #/ml | MDiamCum100 | #/ml >100 use max dia |
| MDiamMaxSize | microns | MDiamMaxSize | Max diam in microns use max dia |
| MDiamMeanSize | microns | MDiamMeanSize | Mean diam in microns use max dia |
| MDiamStdDev | microns | MDiamStdDev | StDev all diams in microns use max dia |
| ISO4 | n/a | ISO4 | ISO44406 >4 microns |
| ISO6 | n/a | ISO6 | ISO44406 >6 microns |
| ISO14 | n/a | ISO14 | ISO44406 >14 microns |
| NAVAIR | n/a | NAVAIR | NAS1638 code |
| CHA(RN) | n/a | CHA(RN) | CHA(RN) code |
| HAL | n/a | HAL | HAL code |
| CDiamCum5 | #/ml | CDiamCum5 | #/ml >5 use eqiv cir |
| CDiamCum15 | #/ml | CDiamCum15 | #/ml >15 use eqiv cir |
| CDiamCum20 | #/ml | CDiamCum20 | #/ml >20 use eqiv cir |
| CDiamCum21 | #/ml | CDiamCum21 | #/ml >21 use eqiv cir |
| CDiamCum25 | #/ml | CDiamCum25 | #/ml >25 use eqiv cir |
| CDiamCum50 | #/ml | CDiamCum50 | #/ml >50 use eqiv cir |
| CDiamCum100 | #/ml | CDiamCum100 | #/ml >100 use eqiv cir |
| WaterIndex | ppmv | WaterIndex | Free water in ppmv |
| CutCum20 | #/ml | CutCum20 | #/ml >20 use max dia cut particles |
| CutCum25 | #/ml | CutCum25 | #/ml >25 use max dia cut particles |
| CutCum50 | #/ml | CutCum50 | #/ml >50 use max dia cut particles |
| CutCum100 | #/ml | CutCum100 | #/ml >100 use max dia cut particles |
| CutMaxSize | microns | CutMaxSize | max dia cut particle in microns |
| SlideCum20 | #/ml | SlideCum20 | #/ml >20 use max dia slide wear particles |
| SlideCum25 | #/ml | SlideCum25 | #/ml >25 use max dia slide wear particles |
| SlideCum50 | #/ml | SlideCum50 | #/ml >50 use max dia slide wear particles |
| SlideCum100 | #/ml | SlideCum100 | #/ml >100 use max dia slide wear particles |
| SlideMaxSize | microns | SlideMaxSize | max dia slide wear particle in microns |
| FatCum20 | #/ml | FatCum20 | #/ml >20 use max dia fatigue wear particles |
| FatCum25 | #/ml | FatCum25 | #/ml >25 use max dia fatigue wear particles |
| FatCum50 | #/ml | FatCum50 | #/ml >50 use max dia fatigue wear particles |
| FatCum100 | #/ml | FatCum100 | #/ml >100 use max dia fatigue wear particles |
| FatMaxSize | microns | FatMaxSize | max dia fatigue wear particle in microns |
| FatCntMean | microns | FatCntMean | max dia fatigue wear particle in microns |

| Property Name | UOM | Description | |
|---|---|---|---|
| FatCntStdDev | microns | FatCntStdDev | mean dia fatigue wear particle in microns use max dia |
| OxideCum20 | #/ml | OxideCum20 | #/ml >20 use max dia oxide particles |
| OxideCum25 | #/ml | OxideCum25 | #/ml >25 use max dia oxide particles |
| OxideCum50 | #/ml | OxideCum50 | #/ml >50 use max dia oxide particles |
| OxideCum100 | #/ml | OxideCum100 | #/ml >100 use max dia oxide particles |
| OxideMaxSize | microns | OxideMaxSize | max dia oxide particle in microns use max dia |
| OtherCum20 | #/ml | OtherCum20 | #/ml >20 use max dia unclassed particles |
| OtherCum25 | #/ml | OtherCum25 | #/ml >25 use max dia unclassed particles |
| OtherCum50 | #/ml | OtherCum50 | #/ml >50 use max dia unclassed particles |
| OtherCum100 | #/ml | OtherCum100 | #/ml >100 use max dia unclassed particles |
| OtherMaxSize | microns | OtherMaxSize | max dia unclassed particles in microns use max dia |
| OtherCntMean | microns | OtherCntMean | mean dia unclassed particles in microns use max dia |
| OtherCntStdDev | microns | OtherCntStdDev | StDev dia unclassed particles in microns use max dia |
| SAE4 | n/a | SAE4 | 4 micron SAE AS4059 code |
| SAE6 | n/a | SAE6 | 6 micron SAE AS4059 code |
| SAE14 | n/a | SAE14 | 14 micron SAE AS4059 code |
| SAE21 | n/a | SAE21 | 21 micron SAE AS4059 code |
| SAE38 | n/a | SAE38 | 38 micron SAE AS4059 code |
| SAE70 | n/a | SAE70 | 70 micron SAE AS4059 code |
| SAEmax | n/a | SAEmax | Max SAE AS4059 code for ranges tested |
| PctSoot | % wt | PctSoot | % soot in oil |
| Kinematic Viscosity(cSt) | cSt | Kinematic Viscosity(cSt) | Kinematic Viscosity(cSt) at 40 C. derived |
| Dynamic Viscosity (cP) | cP | Dynamic Viscosity(cP) | Dynamic Viscosity(cP) at 40 C. measured |
| BSW | n/a | BSW | BSW |
| CFD | n/a | CFD | CFD |
| Fibers | #/ml | Fibers | #/fibers/ml fluid |
| GOST | n/a | GOST | GOST code |

Specific features of the invention are shown in some drawings and not in others, but this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A route based analysis system comprising:
    a device including:
        an oil sample cell;
        an infrared spectrometer subsystem responsive to the oil sample cell and configured to produce a spectrum for oil introduced to the oil sample cell; and a processing subsystem responsive to the infrared spectrometer subsystem and operating computer programs which:
- display a route stored in a computer memory, including assets with oil to be inspected,
- determine the type of oil used in each asset by searching the computer memory,
- locate, for each asset on the route, one or more oil property methods specific to the oil used in the asset stored in the computer memory,
- locate, for each asset along the route, an alarm set specific to the asset stored in the computer memory,
- analyze the spectrum of each asset's oil produced by the infrared spectrometer using said one or more stored specific methods producing oil properties after introducing said oil to the sample cell along the route, and
- compare the oil properties with the stored alarm set specific to the asset; and a display for displaying said oil properties and any alarm indications.

2. The system of claim 1 further including locating, for each asset's oil, a reference spectrum.

3. The system of claim 2 in which analyzing includes using oil property methods which compare said produced spectrum with said reference spectrum.

4. The system of claim 3 in which different oil property methods cover different spectrum wavelength ranges.

5. The system of claim 4 in which different oil property methods include differently weighted functions.

6. The system of claim 1 in which said oil properties include water content, acidity, soot content, the presence of additives, and/or percent oxidation, and/or combinations of the same.

7. The system of claim 6 in which said properties further include, for select assets, a calculated total acid and/or saponification number.

8. The system of claim 7 in which said oil properties include, for other assets, a total base number.

9. The system of claim 1 in which said sample cell is a flip-top sample cell.

10. The system of claim 1 further including a screen for said displays.

11. The system of claim 1 in which the type of oil used in each asset on the route is stored in the system.

12. The system of claim 1 in which said oil property methods are stored in the system.

13. The system of claim 1 in which said alarm sets are stored in the system.

14. A route based analysis system comprising:
a portable handheld unit including:
- an oil sample cell;
- a display screen for displaying a route to specific locations of machines or engines;
- a spectrometer subsystem including an analyzer for producing a spectrum for oil loaded into the oil sample cell from a machine or engine at a said specific location along the route;
- a database with route data, oil property analysis methods and reference spectrums and alarm sets for different types of machines or engines along the route;
- the display screen also for displaying oil properties and any alarm indications for the oil loaded into the sample cell from the machine or engine at the said specific location along the route; and
- a processing subsystem responsive to the spectrometer subsystem and the database for displaying on the display screen the route and the oil properties and alarm indications for the oil loaded into the sample cell from the machine or engine at the said specific location along the route.

15. The system of claim 14 in which the oil properties displayed include water content, acidity, soot content, the presence of additives, and/or percent oxidation, and/or combinations of the same.

16. The system of claim 15 in which the oil properties displayed further include, for select assets, a calculated total acid and/or saponification number.

17. The system of claim 16 in which the oil properties displayed include, for other assets, a total base number.

18. The system of claim 14 in which the type of oil used in each machine or engine on the route is stored in the database.

19. The system of claim 14 further including a processing subsystem in the portable handheld unit, the processing subsystem configured to:
- display the route on the display screen including machines or engines with oil to be inspected,
- determine the type of oil used in each machine or engine,
- locate, for each machine or engine on the route, one or more of the oil property analysis methods specific to the oil used in the machine or engine,
- locate, for each machine or engine along the route, an alarm set specific to the machine or engine,
- analyze the spectrum, for each machine or engine's oil along the route, using said one or more of the specific oil property analysis methods and producing oil properties after the oil is loaded into the sample cell,
- compare the oil properties, for each machine or engine along the route, with the alarm set specific to the machine or engine, and
- display on the display screen the oil properties and any alarm indications.

* * * * *